US010350002B2

(12) United States Patent
Terwey et al.

(10) Patent No.: US 10,350,002 B2
(45) Date of Patent: Jul. 16, 2019

(54) ELECTRODE ASSEMBLY FOR CATHETER SYSTEM

(71) Applicant: St. Jude Medical, Cardiology Division, Inc., St. Paul, MN (US)

(72) Inventors: Russell David Terwey, St. Michael, MN (US); Steve N. Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1423 days.

(21) Appl. No.: 14/258,407

(22) Filed: Apr. 22, 2014

(65) Prior Publication Data
US 2014/0324043 A1 Oct. 30, 2014

Related U.S. Application Data

(60) Provisional application No. 61/816,043, filed on Apr. 25, 2013.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01);
(Continued)

(58) Field of Classification Search
CPC .......... A61B 18/1492; A61B 218/0016; A61B 218/00267; A61B 218/00357;
(Continued)

(56) References Cited

U.S. PATENT DOCUMENTS 3,650,277 A   3/1972  Sjostrand et al.
4,658,819 A   4/1987  Harris et al.
(Continued)

FOREIGN PATENT DOCUMENTS

KR   101399555   5/2014
WO   97/45157    12/1997
(Continued)

OTHER PUBLICATIONS

Millard, F.C. et al, Renal Embolization for Ablation of Function in Renal Failure and Hypertension, Postgraduate Medical Journal (1989) 65, 729-734.

(Continued)

*Primary Examiner* — Michael F Peffley
*Assistant Examiner* — Samantha M Good
(74) *Attorney, Agent, or Firm* — Armstrong Teasdale LLP

(57) ABSTRACT

An electrode assembly for a catheter system has a longitudinal axis, a proximal end and a distal end. Multiple struts extend coextensively with each other from the proximal end to the distal end of the electrode assembly. Each strut carries an electrode spaced longitudinally from the proximal end of the electrode assembly. The longitudinal spacing of one electrode from the proximal end of the electrode assembly is different from the longitudinal spacing of another electrode from the proximal end of the electrode assembly. The electrode assembly is configurable between a collapsed configuration and an expanded configuration, with the electrodes being transversely spaced from the longitudinal axis of the electrode assembly a greater distance in the expanded configuration than in the collapsed configuration. In the expanded configuration, the electrodes are transversely spaced from the longitudinal axis of the electrode assembly approximately the same distance.

14 Claims, 11 Drawing Sheets

(52) U.S. Cl.
CPC ............ *A61B 2018/00357* (2013.01); *A61B 2018/00404* (2013.01); *A61B 2018/00434* (2013.01); *A61B 2018/00577* (2013.01); *A61B 2018/1467* (2013.01)

(58) Field of Classification Search
CPC .... A61B 218/00404; A61B 218/00434; A61B 218/00577; A61B 218/1467; A61B 2018/00267; A61B 2018/1467
See application file for complete search history.

(56) References Cited

U.S. PATENT DOCUMENTS

| | | | |
|---|---|---|---|
| 5,035,694 A | 7/1991 | Kasprzyk et al. | |
| 5,255,679 A | 10/1993 | Imran | |
| 5,300,068 A | 4/1994 | Rosar et al. | |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Mulier et al. | |
| 5,911,739 A * | 6/1999 | Kordis ................. | A61B 5/0422 606/41 |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0107512 A1 | 8/2002 | Edwards | |
| 2002/0120304 A1 | 8/2002 | Mest | |
| 2003/0045898 A1 | 3/2003 | Harrison et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2005/0288730 A1 | 12/2005 | Deem et al. | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2010/0016762 A1 | 1/2010 | Thapliyal et al. | |
| 2010/0076426 A1* | 3/2010 | de la Rama ....... | A61B 18/1492 606/41 |
| 2010/0094209 A1 | 4/2010 | Drasler et al. | |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1* | 5/2011 | De La Rama ..... | A61B 18/1492 606/33 |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |

FOREIGN PATENT DOCUMENTS

| | | |
|---|---|---|
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2011/060339 | 5/2011 |
| WO | 2012/064818 | 5/2012 |
| WO | 2012/106492 | 8/2012 |
| WO | 2013/163411 | 10/2013 |

OTHER PUBLICATIONS

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology,

(56) References Cited

OTHER PUBLICATIONS vol. 216, No. 4, Apr. 1969, 693-697.

Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of the American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oparil, Suzanne et al, Renal Nerve Ablation: Emerging Role in Therapeutics; Blood Pressure, Oct. 2011, vol. 20, No. 5 , pp. 253-255.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, TIME Magazine, Monday, Jan. 9, 2012.

Page, Irvine H. et al, Mechanisms, Diagnosis and Treatment of Hypertension of Renal Vascular Origin, Annal of Internal Medicine, Aug. 1959, vol. 51, No. 2, 196-211.

Page, Irvine H. et al, Mechanisms, Diagnosis and Treatment of Hypertension of Renal Vascular Origin; Annals of Internal Medicine, Aug. 1959;51:196-211.

Page, Irvine H. et al, The Effect of Renal Denervation on the Level of Arterial Blood Pressure and Renal Function in Essential Hypertension, Journal of Clinical Investigation, 1935;14(1):27-30.

Page, Irvine H. et al, The Effects of Renal Denervation on Patients Suffering from Nephritis, J Clin Invest. 1935;14(4):443-458.

Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

Page, Max, Section of Surgery, Discussion on the Surgical Treatment of Hypertension, Proceedings of the Royal Society of Medicine, vol. XLI, Feb. 1948, 359-372.

Papademetriou, Vasilios, Hypertension and the Simplicity Renal Denervation System, Scientific Background, www.niedtronic.com, 2011.

Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3): 139-142.

Persu, Alexandre et al, Renal Denervation: Ultima Ratio or Standard in Treatment-Resistant Hypertension, Hypertension Journal of the American Heart Association, Sep. 2012;60(3):596-606.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of the American Heart Association, 1999;99:319-325.

Plouin, Pierre-Francois et al, Blood Pressure Outcome of Angioplasty in Atherosclerotic Renal Artery Stenosis A Randomized Trial, Hypertension Journal of the American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

(56) References Cited

OTHER PUBLICATIONS

Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4: 1886-1891, 2009.

Robbins, Ivan M. et al, Pulmonary Vein Stenosis After Catheter Ablation of Atrial Fibrillation, Circulation Journal of the American Heart Association, 1998;98:1769-1775.

Rocha-Singh, Krishna J., Catheter-Based Sympathetic Renal Denervation A Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of the American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept, Hypertension Journal of the American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of the American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of the American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of the American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper.-Theory and Practice, Ag(Suppl.I), 47-57 (1987).

(56) References Cited

OTHER PUBLICATIONS

Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of the American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

(56) References Cited

OTHER PUBLICATIONS

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun.), 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of the American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of the American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Dibona, Gerald F., Neural Control of the Kidney: Past, Present, and Future, Hypertension Journal of the American Heart Association, vol. 41, Mar. 2003, Part II, 621-624.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.

(56) References Cited

OTHER PUBLICATIONS

Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of the American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.
Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, A. Neil et al, Endovascular Renal Denervation: A Novel Sympatholytic with Relevance to Chronic Kidney Disease, Clinical Kidney Journal Advance Access, (2013) 0: 1-8.
Huang, K. Shoei Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of the American Heart Association, 1998;32:249-254.
Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Hypertension Reports 1999, 3:254-263.
International Search Report for Application No. PCT/US14/034898 dated Aug. 4, 2014.
Abboud, Francois M., The Sympathetic System in Hypertension, State-of-the-Art Review, Hypertension Journal of the American Heart Association, Hypertension 4 (suppl II):II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, a Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.

(56) References Cited

OTHER PUBLICATIONS

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.

Campese, Vito M., Interventional Hypertension: A New Hope or a New Hype? The Need to Redefine Resistant Hypertension, J Hypertens. Nov. 2013;31(11):2118-21.

Canadian Agency for Drugs and Technologies in Health, Catheter-Based Renal Denervation for Treatment-Resistant Hypertension; Issues in Emerging Health Technologies, Issue 121, Mar. 2013.

Carlstedt, Thomas et al, Regrowth of Lesioned Dorsal Root Nerve Fibers into the Spinal Cord of Neonatal Rats, Neuroscience Letters Feb. 10, 1987;74(1):14-8.

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review—Part II, Journal of the National Medical Association, May 1948, vol. 40, No. 3., 113-116.

Dailey, U.G., Surgical Treatment of Hypertension: A Review—Part III, Journal of the National Medical Association, Jul. 1948, vol. 40, No. 4, 160-162.

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.

De Wardener, H.E., The Hypothalamus and Hypertension, Physiological Reviews, vol. 81, No. 4, Oct. 2001.

Dequattro V. et al, The Sympathetic Nervous System: The Muse of Primary Hypertension, Journal of Human Hypertension, 2002, 16 (Supp) 1), S64-S69.

Dibona, Gerald F. et al, Neural Control of Renal Function, Physiological Reviews, vol. 77, No. 1, Jan. 1997, 75-197.

Dibona, Gerald F. et al, Translational Medicine: The Antihypertensive Effect of Renal Denervation, Americal Journal of Physiology, 2010, 298, R245-R253.

Dibona, Gerald F., Neural Control of Renal Function: Cardiovascular Implications, Hypertension Journal of the American Heart Association, vol. 13, No. 6, Part 1, Jun. 1989, 539-548.

Dibona, Gerald F., Neural Control of the Kidney: Functionally Specific Renal Sympathetic Nerve Fibers, American Journal of Physiology, 2000, 279, R1517-R1524.

Young, Robert R. et al, Reversible Block of Nerve Conduction by Ultrasound Ultrasonic Blocking of Nerve Fibers, Arch Neurol. 1961;4(1):83-89.

Zazgornik, Jan et al, Bilateral Nephrectomy: The Best, but Often Overlooked, Treatment for Refractory Hypertension in Hemodialysis Patients, AJH 1998; 11:1364-1370.

\* cited by examiner

ELECTRODE ASSEMBLY FOR CATHETER SYSTEM

CROSS-REFERENCE TO RELATED APPLICATIONS

This application claims priority to provisional application Ser. No. 61/816,043 filed Apr. 25, 2013, the entire specification of which is incorporated herein.

BACKGROUND OF THE DISCLOSURE

A. Field of the Disclosure

The present disclosure relates generally to a catheter system for use in a human body, and more particularly to a multi-electrode catheter system, and even more particularly to an electrode assembly for a multi-electrode catheter system.

B. Background Art

Catheter systems are well known in the art for use in medical procedures, such as diagnostic, therapeutic and ablative procedures. Typical catheter systems generally include an elongate catheter extending from a handle. A physician manipulates the catheter through the patient's vasculature to an intended site within the patient. The catheter typically carries one or more working components, such as electrodes or other diagnostic, therapeutic or ablative devices for carrying out the procedures. One or more controls or actuators may be provided on the handle for selectively adjusting one or more characteristics of the working components.

One particular example of a multi-electrode catheter system is an ablative catheter system in which the working component is a multi-electrode component carried at the distal end of a flexible catheter. A control wire extends within the catheter from the multi-electrode component to the handle to operatively connect the multi-electrode component to an actuator on the handle. Manipulating the actuator acts on the control wire to configure the multi-electrode component into a desired configuration for carrying out the ablative procedure. For example, in one such ablative catheter system made by St. Jude Medical, Inc. under the trade name EnligHTN, the multi-electrode component is an electrode assembly in the general form of a basket. Upon locating the electrode basket at a desired location within the patient, manipulating the actuator associated with the handle pulls on the control wire to reconfigure the electrode basket from a collapsed configuration to an expanded configuration in which the electrodes are intended to be in apposition with a surface, such as an arterial wall of the patient. It is thus desirable to facilitate apposition of as many of the electrodes of the electrode basket as possible against the arterial wall of the patient when the electrode basket is expanded to achieve optimal performance of the multi-electrode catheter system.

BRIEF SUMMARY OF THE DISCLOSURE

In one embodiment, a catheter system generally comprises a handle, an elongate shaft extending from the handle, and an electrode assembly carried by the shaft and having a longitudinal axis, a proximal end and a distal end. The electrode assembly generally comprises a first strut extending from the proximal end to the distal end of the electrode assembly. The first strut has a first hinge at a first longitudinal distance from the proximal end of the electrode assembly to facilitate bending of the strut at the first hinge. A second strut different from the first strut extends coextensively with the first strut from the proximal end to the distal end of the electrode assembly. The second strut has a second hinge at a second longitudinal distance from the proximal end of the electrode assembly to facilitate bending of the second strut at the second hinge, the second longitudinal distance being different from the first longitudinal distance of the first hinge. The electrode assembly is configurable between a collapsed configuration in which the first and second hinges are at a first transverse distance relative to the longitudinal axis of the electrode assembly, and an expanded configuration in which the first and second hinges are transversely spaced a second transverse distance relative to the longitudinal axis of the electrode assembly, the second transverse distance being greater than the first transverse distance. An actuator associated with the handle is operatively connected to the electrode assembly for selectively configuring the electrode assembly from its collapsed configuration to its expanded configuration.

In another embodiment, an electrode assembly for an electrode catheter system has a longitudinal axis, a proximal end and a distal end. The electrode assembly generally comprises a plurality of struts extending coextensively with each other from the proximal end to the distal end of the electrode assembly. Each strut has a corresponding electrode disposed thereon and spaced longitudinally from the proximal end of the electrode assembly. The longitudinal spacing of one of the electrodes from the proximal end of the electrode assembly is different from the longitudinal spacing of at least another one of the electrodes from the proximal end of the electrode assembly. The electrode assembly is configurable between a collapsed configuration and an expanded configuration, with the electrodes being transversely spaced from the longitudinal axis of the electrode assembly a greater distance in the expanded configuration than in the collapsed configuration. In the expanded configuration, the electrodes are transversely spaced from the longitudinal axis of the electrode assembly approximately the same distance.

In yet another embodiment, an electrode assembly for an electrode catheter system has a longitudinal axis, a proximal end and a distal end, and is configurable between a collapsed configuration and an expanded configuration. The electrode assembly generally comprises a plurality of struts extending coextensively from the proximal end to the distal end of the electrode assembly. Each strut has a length and a respective hinge along its length to facilitate bending of the strut at the respective hinge upon configuration of the electrode assembly from its collapsed configuration to its expanded configuration. Each strut has a first width at the respective hinge, and a second width longitudinally adjacent the respective hinge wherein the first width is substantially less than the second width to define the respective hinge of the strut.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 7a is an enlarged schematic view of one strut of the electrode assembly of FIG. 6;

FIG. 7b is an enlarged schematic of a hinge of the strut of FIG. 7a;

Corresponding reference characters indicate corresponding parts throughout the several views of the drawings.

DETAILED DESCRIPTION OF THE DISCLOSURE

Figure 1:
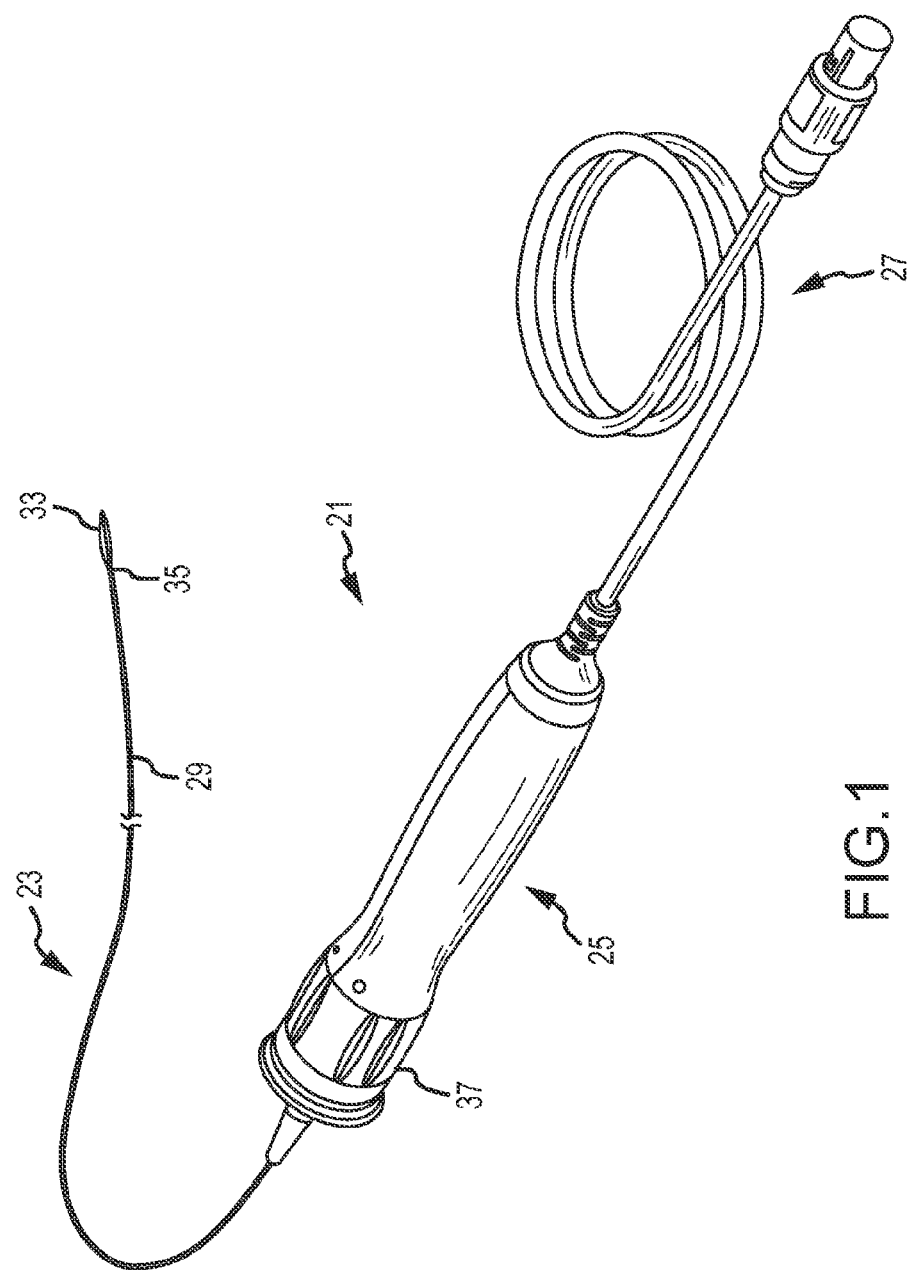
FIG. 1 is a perspective view of one embodiment of a catheter system including a handle, a catheter and an electrode assembly having multiple electrodes, with the electrode assembly being in a collapsed configuration.
Figure 2:
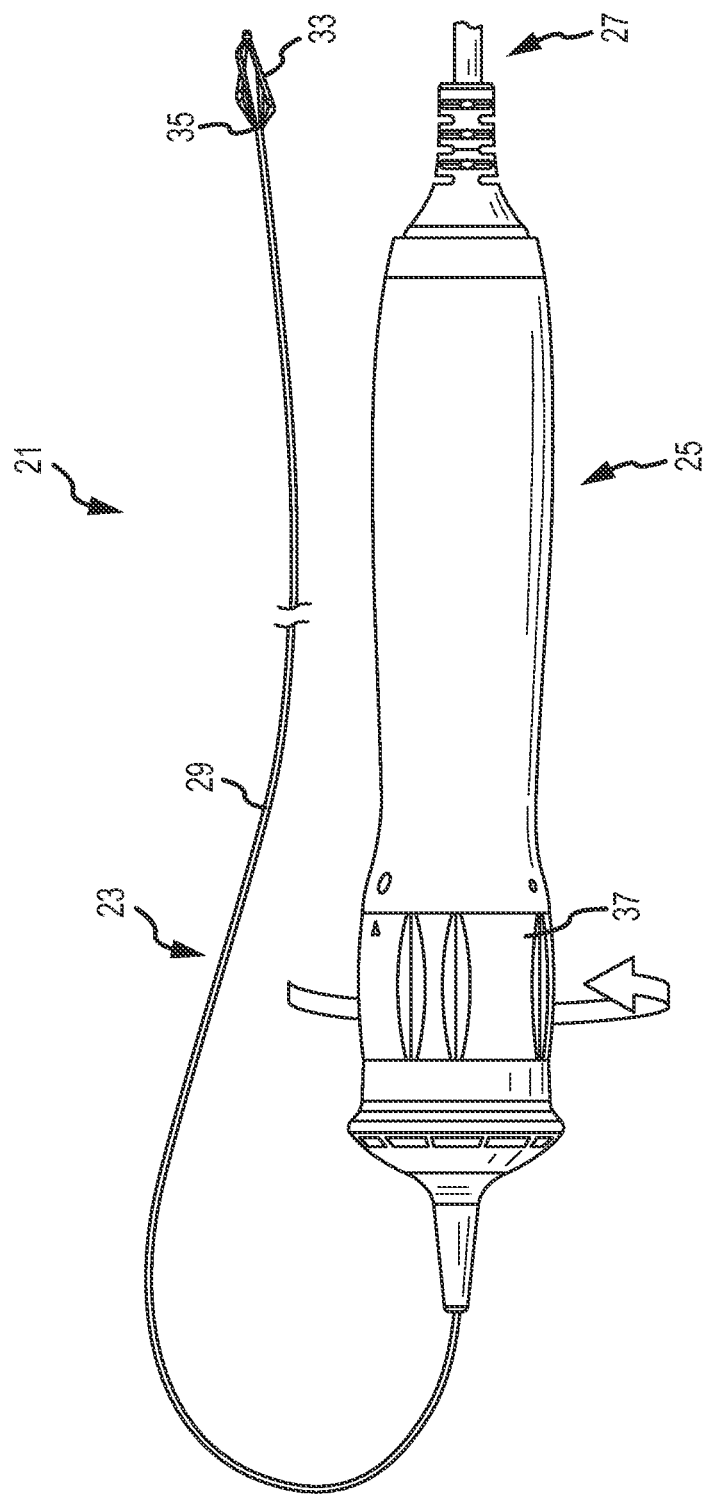
FIG. 2 is a side elevation of the catheter system of FIG. 1, with the electrode assembly being in an expanded configuration resulting from rotation of a rotatable actuator.

Referring now to the drawings, and in particular to FIGS. 1 and 2, one embodiment of a catheter system 21 includes a flexible catheter 23, a handle 25 to which the catheter is connected, and a conductor assembly 27 for electrically connecting the catheter system to a suitable power supply (not shown). As one example, the catheter system 21 illustrated and described herein is suitably constructed for use as an ablation system, such as a renal or heart ablation system. More particularly, the illustrated catheter system 21 is a multi-electrode renal denervation system. One example of such a catheter system 21 is currently made by St. Jude Medical, Inc. under the trade name EnligHTN. General operation of a multi-electrode renal denervation system is known to those of skill in the art and is not described further herein except to the extent necessary to describe the present embodiments. It is also understood that the catheter system 21 may be used for any other suitable treatment or purpose without departing from the scope of this disclosure. Additionally, while the catheter system 21 is illustrated and described herein as including a flexible catheter 23, the system may further include other components used, for example, to guide the flexible catheter into the patient—such as, without limitation, a relatively more rigid guide catheter (not shown).

The catheter 23 includes an elongate, flexible hollow shaft 29 connected to the handle 25 at or near a proximal or rear end of the catheter shaft (not shown because it is hidden by a connector at the front end of the handle 25), and an electrode assembly 33 disposed at or near a distal or front end 35 of the catheter shaft. It is understood, however, that the electrode assembly 33 may be disposed anywhere along the catheter shaft 29 intermediate the proximal end and the distal end 35 thereof without departing from the scope of this disclosure. As used herein, the terms proximal and front, and distal and rear, are used with reference to the orientation of the catheter system 21 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to the handle 25 while the terms distal and front refer to a longitudinal position that is relatively further from the handle.

The illustrated electrode assembly 33 is in the form of what may be referred to as an electrode basket and is suitably configurable between a collapsed configuration (FIG. 1) for maneuvering and positioning the electrode assembly in the patient, and an expanded configuration (FIG. 3) for operation of the electrode assembly to perform a desired procedure such as an ablation procedure. An annular (e.g., ring-shaped) actuator 37 is mounted on the handle 25 for rotation relative thereto and is operatively connected to the electrode assembly 33 for selectively configuring the electrode assembly between its collapsed and expanded configurations. It is understood that another suitable actuator (e.g., slide, push button, lever, etc.) may be used instead of the rotating actuator 37 to selectively configure the electrode assembly 33 without departing from the scope of this disclosure. In some embodiments, the electrode assembly 33 may be selectively adjustable between an infinite number of configurations (e.g., degrees of expansion) between its collapsed and expanded configurations using the actuator 37.

A control line, such as a suitable cable or pull wire 41 (FIG. 3) extends from the electrode assembly 33 within the hollow catheter shaft 29 and into the handle 25 for operative connection with the actuator to thereby operatively connect the actuator 37 with the electrode assembly. In some embodiments two or more pull wires, cables or other suitable control lines may be used for selectively configuring the electrode assembly 33. It is also understood that the control line 41 may be any suitable control line other than a pull wire, such as a cable, string, tie, compression member or other suitable control to operatively connect the electrode assembly 33 to the actuator 37. A suitable twisted electrical wire bundle (not shown) also extends through the hollow catheter shaft 29 from the handle to the electrode assembly to deliver power to the electrode assembly.

Figure 3:
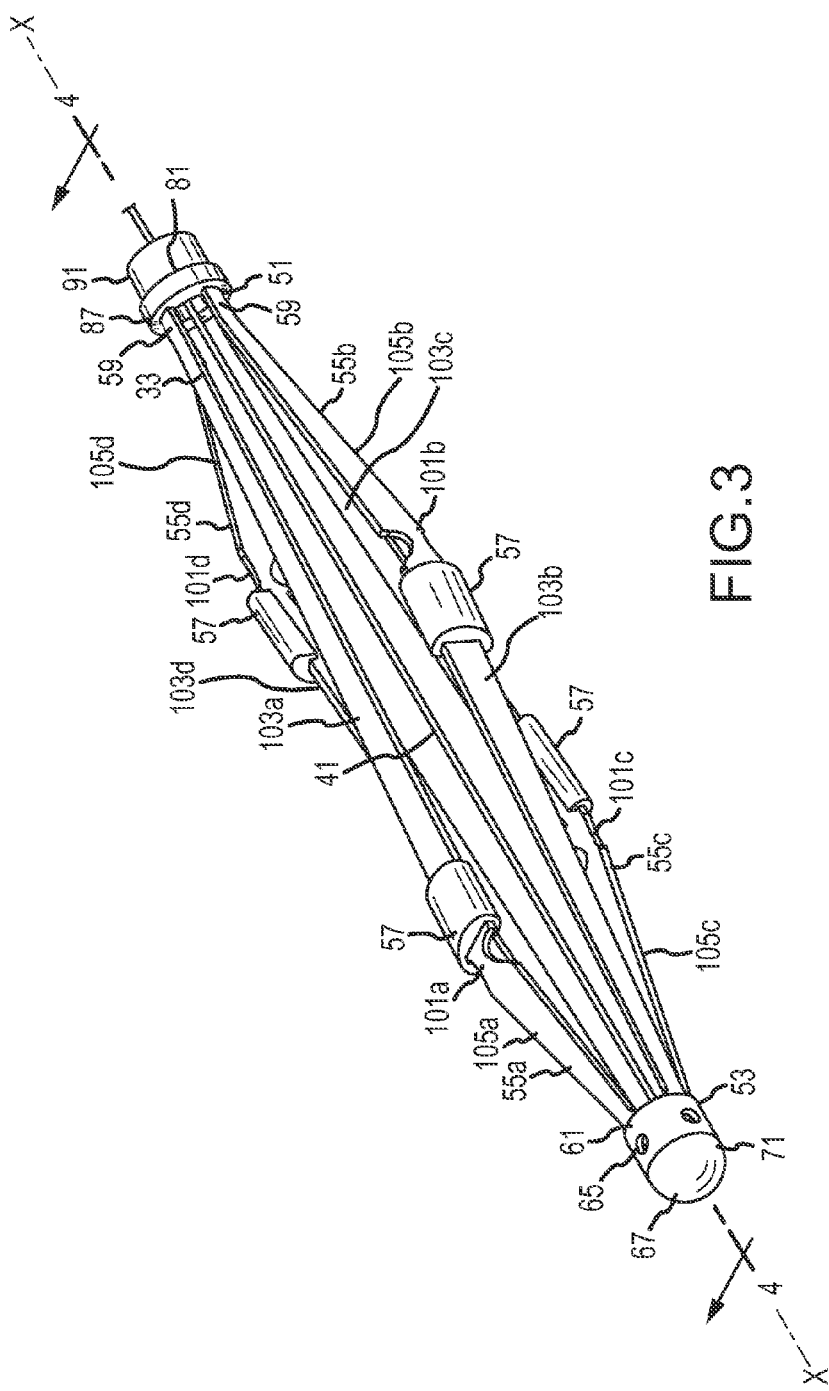
FIG. 3 is a perspective view of the electrode assembly of FIG. 1 separated from the catheter, with a plurality of coextensive struts carrying the multiple electrodes.
Figure 4:
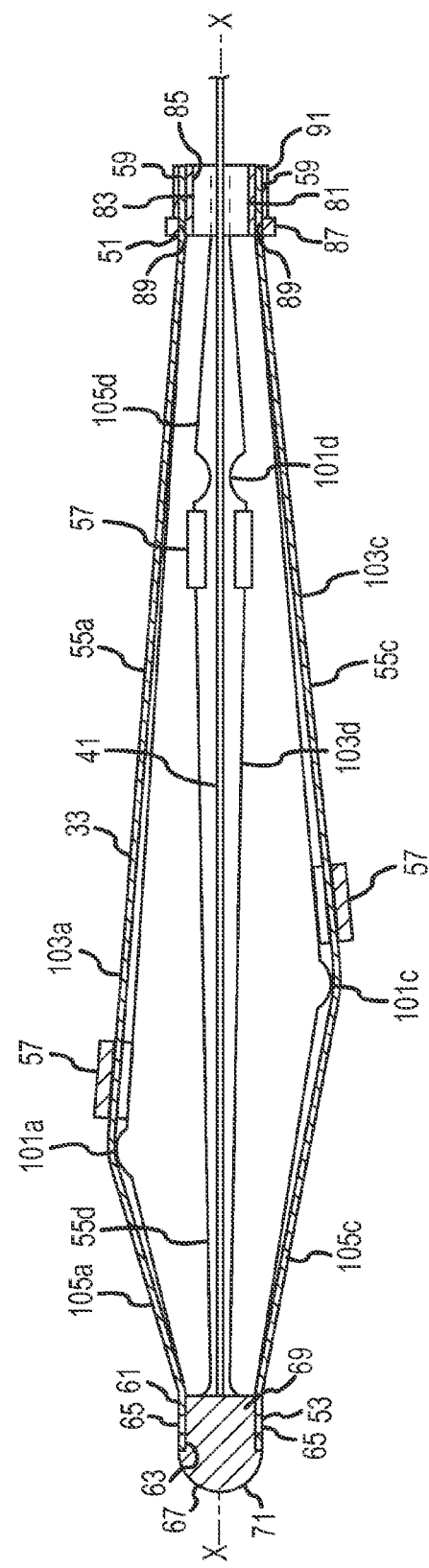
FIG. 4 is a longitudinal cross-section of the electrode assembly of FIG. 3.
Figure 5:
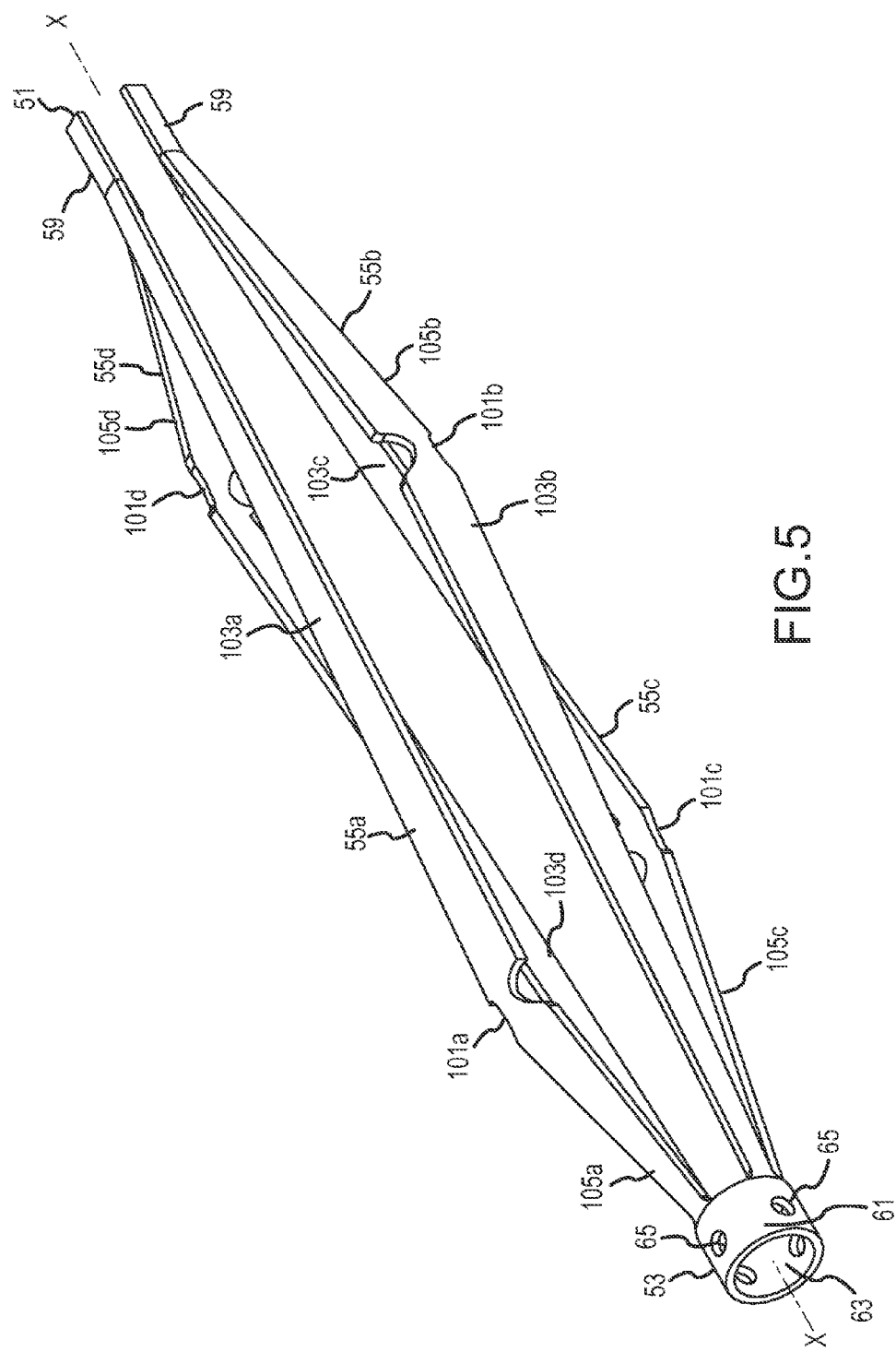
FIG. 5 is a perspective view similar to FIG. 3, with the electrodes, a tip and a coupling of the electrode assembly omitted.

With reference now to FIGS. 3 and 4, the electrode assembly 33 has a proximal end 51 at which the assembly is connected to the catheter shaft 29 (e.g., to the distal end 35 of the catheter shaft in the embodiment of FIGS. 1 and 2), a distal end 53 that in the illustrated embodiment also defines a distal end, or tip, of the catheter 23, and a longitudinal axis X. The illustrated electrode assembly 33 comprises a set of four struts 55a-d, extending coextensively with each other from the proximal end 51 to the distal end 53 of the electrode assembly in circumferentially equal spaced relationship with each other about the longitudinal axis X of the electrode assembly. In other embodiments, the electrode assembly 33 may comprise more or less than four struts 55a-d without departing from the scope of this disclosure. It is also contemplated that the struts 55a-d may be other than equally spaced from each other circumferentially, and/or the struts may be other than coextensive with each other, and remain within the scope of this disclosure.

Each of the struts 55a-d carries at least one electrode 57 disposed at a respective longitudinal position along the strut, i.e., at a respective longitudinal distance along the longitudinal axis X from the proximal end of the electrode assembly. In the embodiment of FIG. 3, each of the electrodes 57 is at a different longitudinal position. It is understood, however, that two, three or all of the electrodes 57 may be at the same longitudinal position. It is also understood that multiple electrodes 57 may be carried by any one or all of the struts 55a-d, e.g., with the electrodes on any given strut spaced longitudinally from each other along the strut. While not illustrated herein, one or more suitable sheathing or sleeves, constructed of a polymeric material, circumferentially enclose each of the struts along their respective lengths. The segment of the control line 41 that extends from the proximal end to the distal end of the electrode assembly may likewise be circumferentially enclosed by a suitable polymeric sheathing or sleeve.

At the distal end 53 of the electrode assembly 33, the struts 55a-d terminate at, and in one embodiment for making the electrode assembly (which is described in further detail later herein) are formed integrally with, a connecting ring 61 having a central opening 63 that is coaxial with the longitudinal axis X of the electrode assembly. Multiple holes 65 are formed in the sidewall of the connecting ring 61 in spaced relationship with each other about the circumference of the connecting ring and are open to the central opening 63 of the connector. Suitable polymeric sheathing (not shown) may surround the connecting ring 61 to cover the holes 65 following assembly of the electrode assembly 33. As seen in FIGS. 3 and 4, a blunt tip 67 includes a cylindrical body 69 having a longitudinal channel extending therethrough, and a rounded head 71 formed integrally with the body at the longitudinally outer end of the body so as to close the longitudinal channel.

The control line 41 extends generally along the longitudinal axis X of the electrode assembly 33 into the longitudinal channel of the body 69 of the tip 67 where it is secured to the tip by braising, adhesive, or other suitable securement technique. The tip body 69 is sized in transverse cross-section, e.g., outer diameter, to be received through and seat within the central opening 63 of the connecting ring 61 with the head 71 of the tip 67 abutting against the end of the connecting ring. The holes 65 spaced about the circumference of the connecting ring 61 allow a suitable adhesive to be supplied through the holes for securing the tip 67 on the connecting ring—thereby connecting the distal end 53 of the electrode assembly 33 to the control line 41 for operative connection with the actuator 37 on the handle 25. In other embodiments the struts 55a-d may be retained at the distal end 53 of the electrode assembly 33 in another suitable manner and remain within the scope of this disclosure. It is also contemplated that the struts 55a-d and connecting ring 61 may be formed separate from each other and subsequently secured together by any suitable securement technique.

At the proximal end 51 of the electrode assembly 33, longitudinal end segments 59 of the struts 55a-d are connected to the catheter shaft 29 by a suitable bushing 81. The bushing 81 includes a cylindrical body 83 having a longitudinal channel 85 through which the control line 41 extends from the catheter shaft 29 to the electrode assembly 33. An annular flange 87 extends radially outward from the longitudinally outer end of the bushing 81. The flange 87 has four slots 89 (corresponding to the respective longitudinal end segments 59 of the struts 55a-d) extending longitudinally therethrough radially outward of the cylindrical body 83 of the bushing 81 and in circumferentially spaced relationship with each other. As illustrated in FIG. 4, the longitudinal end segments 59 of the struts 55a-d extend through the respective slots 89 and along the outer surface of the cylindrical body 83 of the bushing 81.

The body 83 of the bushing 81 (along with the longitudinal end segments 59 of the struts 55a-d) is fitted with a polyimide sleeve 91 filled with suitable adhesive to secure the sleeve and longitudinal end segments of the struts to the bushing. The bushing 81, struts 55a-d and polyimide sleeve 91 are inserted into the distal end 35 of the hollow catheter shaft 29 and secured to the catheter shaft by suitable adhesive to secure the proximal end 51 of the electrode assembly 33 to the distal end of the catheter shaft. It is understood that the struts 55a-d may be connected to the catheter shaft 29 by any other suitable connection that allows the electrode assembly 33 to function in the manner described herein.

Figure 8:
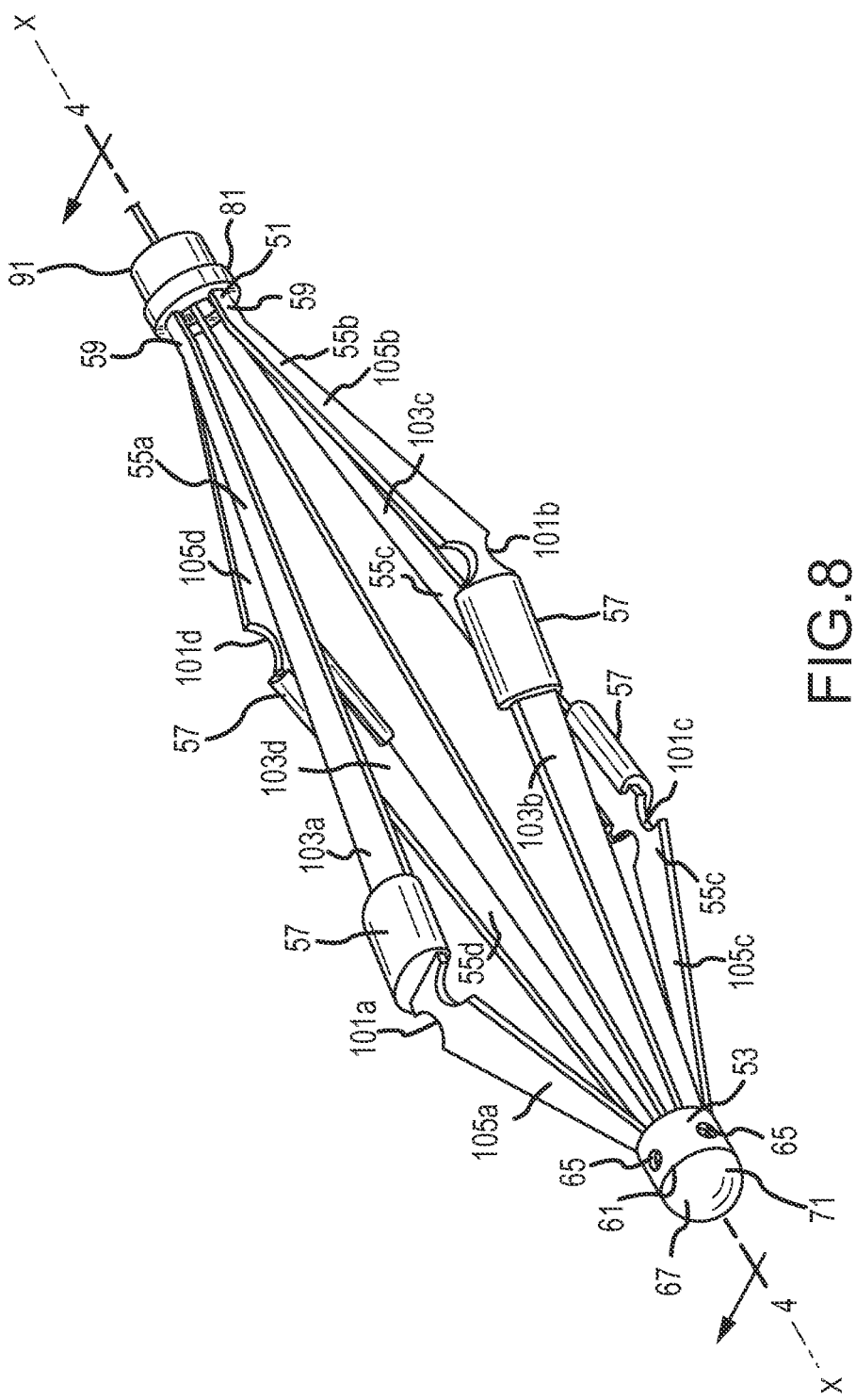
FIG. 8 is a perspective view similar to FIG. 3 but with the electrode assembly illustrated in its expanded configuration.
Figure 9:
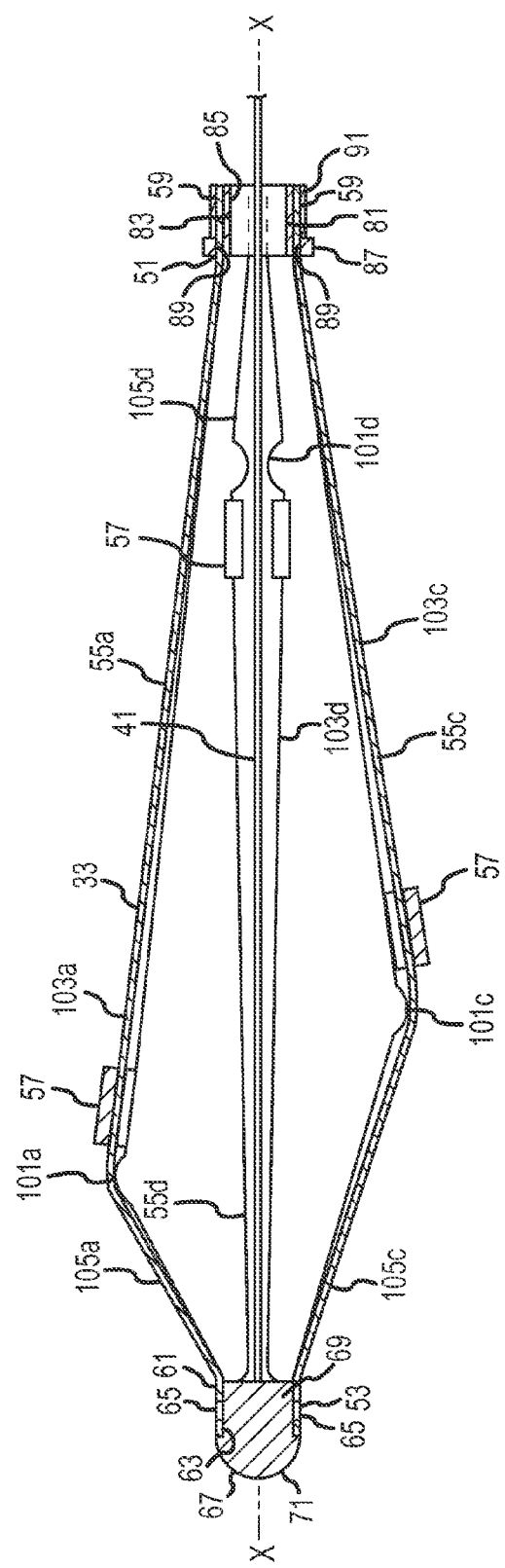
FIG. 9 is a longitudinal cross-section of the electrode assembly of FIG. 8.

The electrode assembly 33 thus has a length defined by the distance along the longitudinal axis X from the proximal end 51 to the distal end 53 of the electrode assembly. To configure the electrode assembly 33 from its collapsed configuration (e.g., as illustrated in FIGS. 1, 3 and 4) to its expanded configuration (e.g., as illustrated in FIGS. 2, 8 and 9), rotation of the actuator 37 relative to the handle 25 operatively pulls on the control wire 41 to thereby pull the tip (i.e., the distal end 53) of the electrode assembly toward the proximal end 51 of the electrode assembly along the longitudinal axis X thereof. As the distance between the distal end 53 and the proximal end 51 of the electrode assembly 33 is shortened (i.e., as the length of the electrode assembly decreases), the struts 55a-d are longitudinally compressed and thus forced to bend, or flex transversely outward away from the longitudinal axis X of the electrode assembly to form the expanded configuration of the electrode assembly. As used herein, the expanded configuration of the electrode assembly refers to any transverse movement of the struts 55a-d outward from the collapsed configuration of the electrode assembly, and may be variably adjusted. Accordingly, it is understood that in the expanded configuration the electrode assembly 33 may be expanded more or less than as illustrated in the various embodiments herein.

In accordance with one embodiment, each of the struts 55a-d has a hinge 101a-d adjacent the respective electrode 57 carried by the strut to facilitate bending of the strut at the hinge upon configuration of the electrode assembly 33 toward its expanded configuration. This provides a predictable bending of the struts 55a-d and thus a predictable and repeatable positioning of the electrodes 57 in the expanded configuration of the electrode assembly. Because the electrodes 57, (as discussed above and illustrated in FIG. 3) are at different longitudinal positions along the length of the electrode assembly 33, the hinges 101a-d for the struts 55a-d are likewise at different longitudinal positions along the length of the electrode assembly. By facilitating bending of the struts 55a-d at the respective hinges 101a-d, in the expanded configuration of the electrode assembly 33 the hinge of each strut is transversely spaced from the longitudinal axis X a distance greater than any other point or segment along the strut. Thus, it will be understood that for each strut 55a-d the hinge 101a-d allows the electrode 57 carried by the strut to be positioned transversely outward away from the longitudinal axis X as much as possible in the expanded configuration of the electrode assembly 33, irrespective of the longitudinal position of the electrode relative to the proximal end 51 of the electrode assembly.

Figure 6:
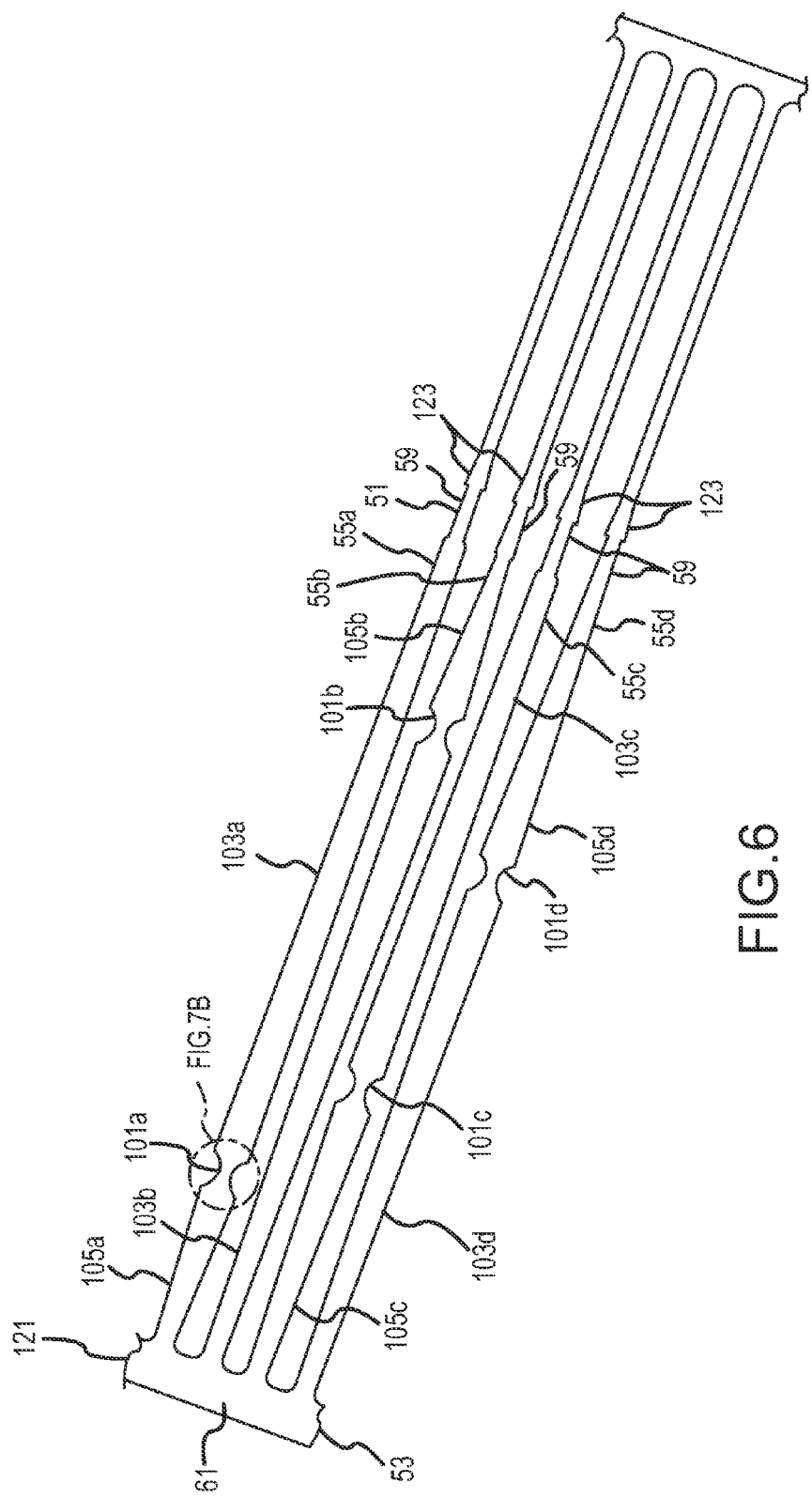
FIG. 6 is a schematic view of the electrode assembly at one stage of manufacturing thereof at which the electrode assembly is in the form of a tube with portions of the tube cut away to form struts of the electrode assembly—the tube being in a longitudinally opened and laid flat orientation for illustrative purposes.

With reference to FIG. 6 solely for purposes of describing the configuration of each of the struts 55a-d, each strut includes a respective longer leg 103a-d and a shorter leg 105a-d—with the respective hinge 101a-d of the strut being disposed at the junction of the longer leg with the shorter leg. In the illustrated embodiment, for example, the topmost strut 55a in FIG. 6 has the longer leg 103a extending from the proximal end 51 of the electrode assembly 33 to the hinge 101a for that strut, and the shorter leg 105a extending from the distal end 53 of the electrode assembly to the hinge. The strut 55b that in the electrode assembly 33 is circumferentially adjacent to the strut 55a has the longer leg 103b extending from the distal end 53 of the electrode assembly 33 to the hinge 101b for that strut and the shorter leg 105b extending from the proximal end 51 of the electrode assembly to the hinge.

Thus, it will be seen in the embodiment of FIGS. 3-9 that the struts 55a-d circumferentially alternate which of the longer or shorter legs 103a-d, 105a-d extends from the proximal end 51 of the electrode assembly 33. This facilitates the struts 55a-d being capable of closely spaced relationship with each other upon compressing down of the electrode assembly 33 (e.g., from its collapsed configuration) as the catheter 23 is guided through the vasculature of the patient. It is understood, however, that the struts 55a-d may be arranged circumferentially about the electrode assembly 33 in any arrangement of which of the longer legs 103a-d or shorter legs 105a-d extend from the proximal end 51 of the electrode assembly. It is also contemplated that in other embodiments the longer legs 103a-d of the struts 55a-d may all extend from the proximal end 51 of the electrode assembly 33, or all extend from the distal end 53 of the electrode assembly, without departing from the scope of this disclosure. As illustrated in FIG. 3, the electrodes 57 carried by the struts 55a-d are each disposed on the longer legs 103a-d of the struts adjacent the respective hinge 101a-d. For example, in one embodiment the electrodes are disposed on the longer legs 103a-d of the struts 55a-d within about 0.03 inches of the respective hinge 101a-d.

With reference to FIGS. 7a and 7b, which illustrates the topmost strut 55a of the electrode assembly 33 of FIG. 6, the longer leg 103a-d of each strut has a width that decreases continuously (e.g., narrows) from a first end 111 adjacent the hinge 101a of the strut to a second end 113 opposite the first end. For example, the longer leg 103a of the strut 55a of FIG. 7a has a width $W_{L1}$ adjacent the hinge 101a and tapers down to a narrower width $W_{L2}$ at the opposite end 113 adjacent the proximal end 51 of the electrode assembly 33. The shorter leg 105a of each strut 55a also has a width that decreases continuously from a first end 115 adjacent the hinge 101a of the strut to a second end 117 opposite the first end. For the strut 55a of FIG. 7a, the shorter leg 105a has a width $W_{S1}$ adjacent the hinge 101a and tapers to a narrower width $W_{S2}$ at the opposite end 117 adjacent the distal end 53 of the electrode assembly 33. The larger width $W_{S1}$ of the shorter leg 105a (e.g. adjacent the hinge 101a) is substantially equal to the larger width $W_{L1}$ of the longer leg 103a. In contrast, the smaller width $W_{S2}$ of the shorter leg 105a is substantially less than the smaller width $W_{L2}$ of the longer leg 103a. Thus, it will be understood that the width of the shorter leg 105a narrows more rapidly along its length than does the width of the longer leg 103a, and the shorter leg narrows down to a smaller width than does the longer leg.

Each strut (as illustrated on the strut 55a in FIG. 7b) has a substantially narrowed width Wz to define the hinge 101a of the strut. As used herein, the width Wz of the strut 55a-d at the hinge 101a-d is defined as a reduced total width of the strut material transversely across the strut. For example, with reference to the hinge 101a of the strut 55a of FIG. 7b, each hinge 101a has U-shaped cut-outs on opposite sides of the respective strut so that the strut material is continuous across along a narrowed width Wz of the hinge. The rounded contour of each of the cut-outs reduces the stress at the hinge 101a upon bending of the strut 55a. In other embodiments, the cut-outs may be other than U-shaped, such as V-shaped or other suitable shape and remain within the scope of this disclosure. It is also understood that the hinge 101a may alternatively be formed by cutting an opening (not shown) between the side edges of the strut 55a at the hinge so that the narrowed width Wz of the strut at the hinge is defined by the combined widths of the webs of strut material remaining on both sides of the opening.

Figure 7:
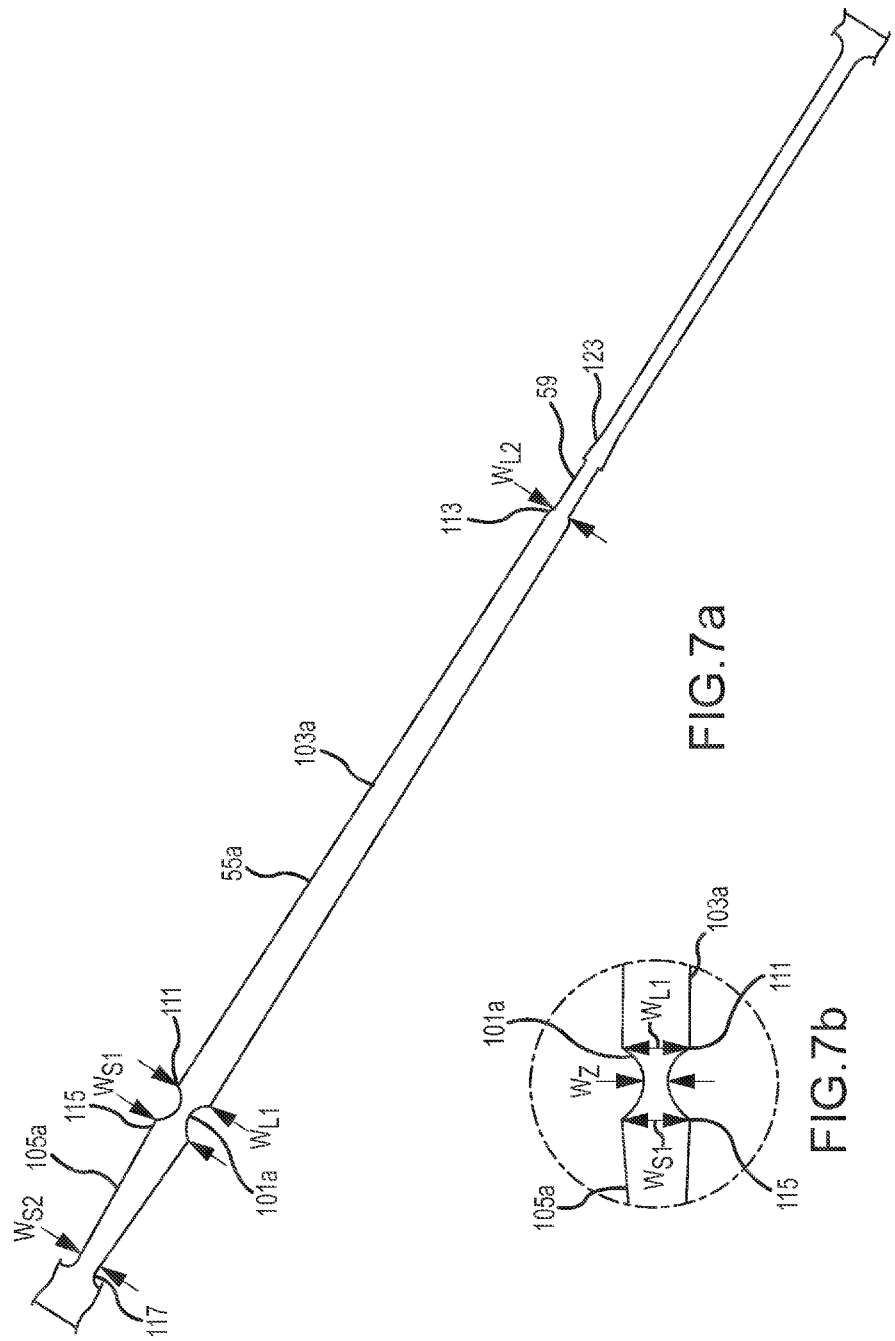

In one example, for the struts 55a-d of the electrode assembly 33 illustrated in FIGS. 3-9, each of the longer legs 103a-d has a width $W_{L1}$ (as illustrated in FIGS. 7a and 7b) adjacent the respective hinge 101a-d of about 0.03 inches. Each of the shorter legs 105a-d has a width $W_{S1}$ adjacent the hinge 101a-d that is approximately equal to the width $W_{L1}$ of the longer leg 103a-d. The width Wz (as illustrated in FIG. 7b) of each strut 55a-d at the respective hinge 101a-d is about 0.01 inches. Additionally, the width of the longer leg 103a-d at the end 113 away from the hinge 101a-d is about 0.02 inches, while the width of the shorter leg 105a-d at the end 117 away from the hinge is about 0.01 inches. It is understood, however, that the relative widths of the longer legs 103a-d, the shorter legs 105a-d and/or the hinges 101a-d may be other than as set forth above and remain within the scope of this disclosure.

In one exemplary embodiment for making the electrode assembly 33 of FIGS. 3-9, a unitary tube 121 of a material having sufficient strength and shape memory characteristics, such as Nitinol™, is used. The illustrated tube 121, as an example, has an outer diameter of about 0.0505 inches and an inner diameter of about 0.042 inches. However, the dimensions of the tube 121 as well as the material or materials from which it is constructed may be other than as set forth above and remain with the scope of this disclosure. The desired pattern of struts 55a-d is then laser cut into the tube 121.

The tube 121 is initially longer than the length of the finished electrode assembly 33 (as illustrated in FIG. 3). For example, the electrode assembly 33 illustrated in FIG. 6 is representative of the tube 121 (although cut lengthwise and laid flat) as initially formed. In the illustrated embodiment, an initial slight amount of preset bend—at the respective hinges 101a-d—is formed in the tube 121 following laser cutting using an internal and external die assembly and then heat set to give the tube its shape memory. Additional preset bending may be heat set into the struts 55a-d adjacent the proximal and/or distal ends 51, 53 of the electrode assembly 33 to further facilitate predictable bending of the struts into their desired configurations in the expanded configuration of the electrode assembly.

As further illustrated in FIG. 6, an alignment member 123 is formed on each strut 55a-d during the laser cutting process longitudinally outward of the ends of the struts near what eventually becomes the proximal end 51 of the electrode assembly 33. Following the heat setting, the tube 21 is cut adjacent the alignment members 123 to define the longitudinal end segments 59 of the struts 55a-d for connecting the struts to the bushing 81 and subsequently to the catheter shaft 29 in the manner described previously. The tip 67 is secured to the distal end 53 of the electrode assembly 33 (e.g., to the connecting ring 61) in the manner described previously.

Figure 10:
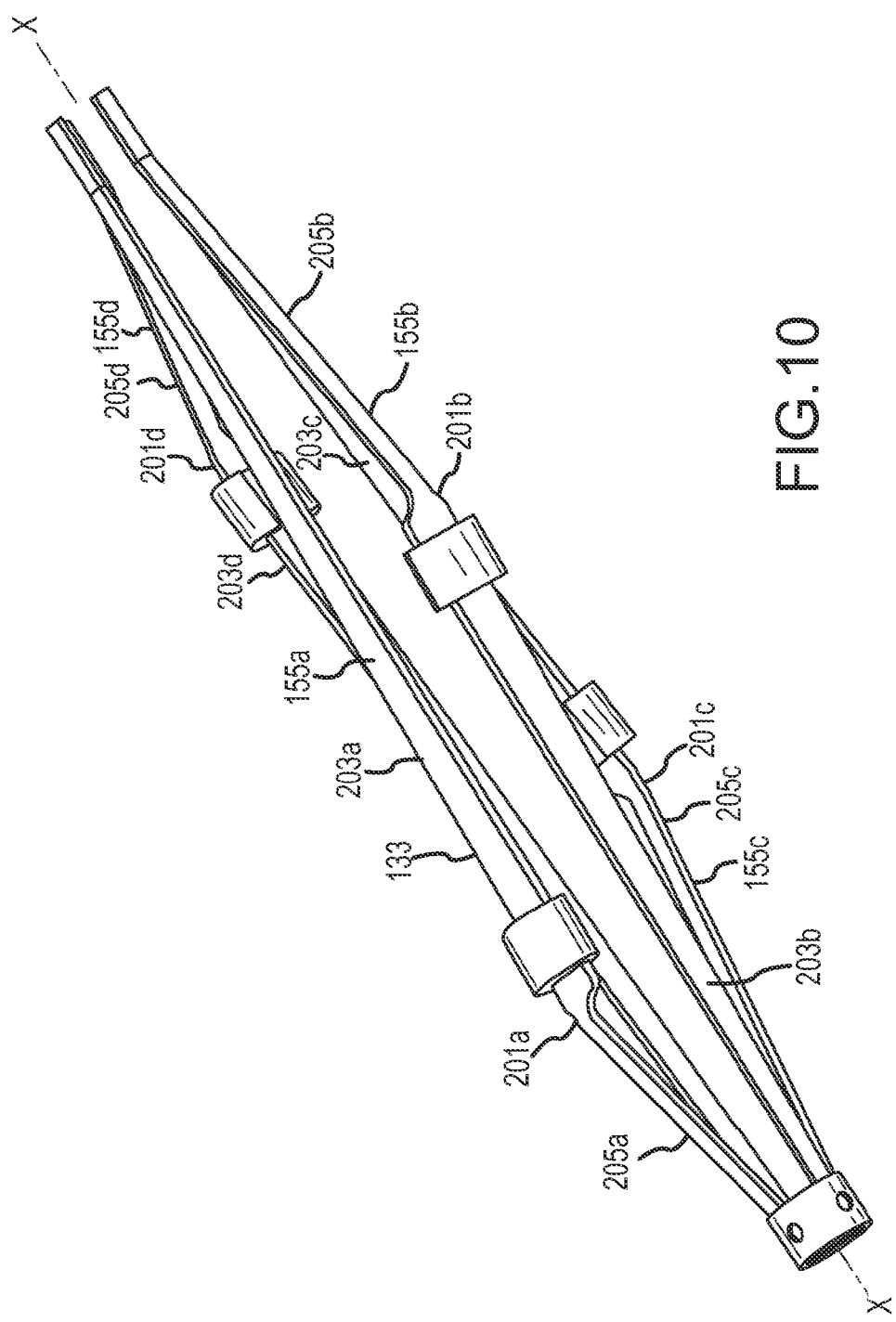
FIG. 10 is a perspective view of another embodiment of an electrode assembly for use with the catheter system of FIG. 1.
Figure 11:
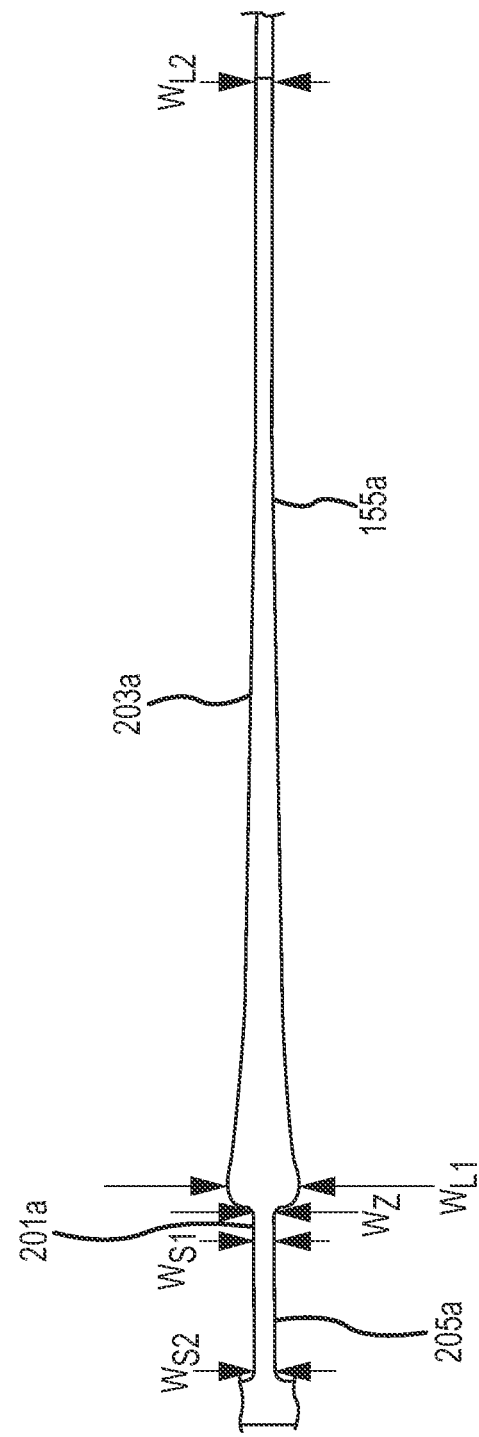
FIG. 11 is a top plan view of one strut of the electrode assembly of FIG. 10, with the strut laid flat for illustrative purposes.

FIGS. 10 and 11 illustrate another embodiment of an electrode assembly 133 suitable for use with a catheter system such as the catheter system 21 illustrated in FIGS. 1 and 2. In this embodiment, the longer legs 203a-d of each of the struts 155a-d are configured to be similar to the longer legs 103a-d of the struts 55a-d of FIGS. 3-9 in that the width $W_{L1}$ of each longer leg is greater adjacent the hinge 201a-d than the width $W_{L2}$ at its end opposite the hinge. In this embodiment, the longer leg 203a-d may be shaped slightly different adjacent the hinge 201a-d than the longer leg 103a-d of each strut 55a-d of the previous embodiment. Alternatively, the longer leg 203a-d adjacent the hinge 201a-d may be shaped substantially the same as the longer leg 103a-d of each strut 55a-d of the previous embodiment, or it may be shaped in any other manner that allows the struts to function in the manner described herein. The shorter leg 205a-d of each strut 155a-d is configured to have a uniform width $W_{S1}$, $W_{S2}$ along its length, including adjacent the hinge 201a-d. For example, in the illustrated embodiment the width $W_{S1}$ of the shorter leg 205a-d adjacent the hinge 201a-d is equal to the width Wz of the strut 155a-d at the hinge.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter system comprising:
a handle,
an elongate shaft extending from the handle
an electrode assembly carried by the shaft and having a longitudinal axis, a proximal end and a distal end, the electrode assembly comprising:
at least two first struts extending from the proximal end to the distal end of the electrode assembly, each of the at least two first struts having a respective first hinge to facilitate bending of each of the at least two first struts at the respective first hinge of each of the at least two first struts; and
a second strut different from the at least two first struts and extending coextensively with the at least two first struts from the proximal end to the distal end of the electrode assembly, the second strut having a second hinge to facilitate bending of the second strut at the second hinge, the second strut interposed between the at least two first struts such that each of the at least two first struts are adjacent the second strut,
wherein a longitudinal spacing of each of the respective first hinge on each strut of the at least two first struts from the proximal end of the electrode assembly is different from a longitudinal spacing of the second hinge on the second strut from the proximal end of the electrode assembly,
the electrode assembly being configurable between a collapsed configuration in which each of the first hinge of the at least two first struts and the second hinge of the second strut are at a first transverse distance relative to the longitudinal axis of the electrode assembly, and an expanded configuration in which each of the first hinge of the at least two first struts and the second hinge of the second strut are transversely spaced a second transverse distance relative to the longitudinal axis of the electrode assembly, the second transverse distance being greater than the first transverse distance; and
an actuator associated with the handle and operatively connected to the electrode assembly for selectively configuring the electrode assembly from its collapsed configuration to its expanded configuration.

2. The catheter system of claim 1 wherein in the collapsed configuration of the electrode assembly the second transverse distance at which each of the first hinge of the at least two first struts is transversely spaced from the longitudinal axis is substantially equal to the second transverse distance at which the second hinge is transversely spaced from the longitudinal axis.

3. The catheter system of claim 1 wherein in the collapsed configuration the first transverse distance of each of the first hinge of the at least two first struts and the second hinge of the second strut relative to the longitudinal axis is greater than zero.

4. The catheter system of claim 3 wherein the at least two first struts and the second strut each respectively comprise a first leg and a second leg, each of the first legs having a first end adjacent the proximal end of the electrode assembly and a second end adjacent the respective one of the first and second hinge, each of the second legs having a first end adjacent the distal end of the electrode assembly and a second end adjacent the respective one of the first and second hinge, the second end of each of the first legs having a width across said first legs, the second end of each of the second legs having a width across said second legs, each of the first and second struts having a width at the hinges that is substantially less than at least one of the width of the second end of each of the first legs and the width of the second end of each of the second legs.

5. The catheter system of claim 1 further comprising at least one electrode disposed on each of the first struts generally adjacent each of the first hinges and at least one electrode disposed on the second strut generally adjacent the second hinge.

6. The catheter system of claim 1 wherein each of the first and second struts comprises a longer leg and a shorter leg, each of the first and second hinges being intermediate the longer leg and the shorter leg to facilitate bending of the strut intermediate the longer and shorter legs.

7. The catheter system of claim 6 further comprising at least one electrode disposed on the longer leg of the first strut generally adjacent each of the first hinges and at least one electrode disposed on the longer leg of the second strut generally adjacent the second hinge.

8. The catheter system of claim 1 wherein the electrode assembly has a length from its proximal end to its distal end, the length of the electrode assembly decreasing upon actuation of the actuator to configure the electrode assembly from its collapsed configuration to its expanded configuration.

9. An electrode assembly for an electrode catheter system, the electrode assembly having a longitudinal axis, a proximal end and a distal end, the electrode assembly comprising:

a plurality of struts comprising a plurality of first and second struts extending coextensively with each other from the proximal end to the distal end of the electrode assembly, each first strut of the plurality of first struts being disposed opposite another first strut of the plurality of struts across the longitudinal axis and each of the plurality of second struts being disposed opposite another of the second struts of the plurality of second struts across the longitudinal axis, each of the plurality of struts having a respective hinge and a corresponding electrode disposed adjacent the respective hinge and spaced longitudinally from the proximal end of the electrode assembly, the longitudinal spacing of each respective electrode on each strut of the plurality of first struts from the proximal end of the electrode assembly being different from the longitudinal spacing of each electrode on each of the plurality of second struts from the proximal end of the electrode assembly;

wherein the electrode assembly is configurable between a collapsed configuration and an expanded configuration, the electrodes being transversely spaced from the longitudinal axis of the electrode assembly a greater distance in the expanded configuration than in the collapsed configuration, in the expanded configuration, the electrodes being transversely spaced from the longitudinal axis of the electrode assembly approximately a same distance.

10. The electrode assembly of claim 9 wherein each strut of the plurality of struts is configured to facilitate bending of the respective strut of the plurality of struts generally adjacent the longitudinal position of the corresponding electrode disposed on the respective strut of the plurality of struts.

11. The electrode assembly of claim 10 wherein each strut of the plurality of struts has a first leg and a second leg and is configured to facilitate bending of the respective strut of the plurality of struts intermediate the first and second legs, the first leg having a first end adjacent the proximal end of the electrode assembly and a second end generally adjacent the second leg, the second end of the first leg having a width across said first leg, the second leg having a first end adjacent the distal end of the electrode assembly and a second end generally adjacent the first leg, the second end of the second leg having a width across said second leg, each strut of the plurality of struts having a width intermediate the second ends of the first and second legs that is substantially less than at least one of the width of the second end of the first leg and the width of the second end of the second leg.

12. The electrode assembly of claim 9 wherein each strut of the plurality of struts comprises a longer leg and a shorter leg, each strut of the plurality of struts being configured to facilitate bending of the corresponding strut of the plurality of struts intermediate the longer leg and the shorter leg.

13. The electrode assembly of claim 12 wherein the corresponding electrode on each strut of the plurality of struts is disposed on the longer leg of the corresponding strut of the plurality of struts.

14. The electrode assembly of claim 9 wherein the electrode assembly has a length from its proximal end to its distal end, the length of the electrode assembly decreasing upon configuring of the electrode assembly from its collapsed configuration to its expanded configuration.

* * * * *